United States Patent [19]

Kimm et al.

[11] Patent Number: 5,161,525

[45] Date of Patent: Nov. 10, 1992

[54] SYSTEM AND METHOD FOR FLOW TRIGGERING OF PRESSURE SUPPORTED VENTILATION

[75] Inventors: Gardner J. Kimm, Carlsbad; Glen N. Gee, Encinitas; Paul J. Fennema, Fallbrook; Warren G. Sanborn, Escondido, all of Calif.

[73] Assignee: Puritan-Bennett Corporation, Carlsbad, Calif.

[21] Appl. No.: 522,383

[22] Filed: May 11, 1990

[51] Int. Cl.$^5$ .................. A61M 16/00; A62B 7/04; F16K 31/02; F16K 31/26

[52] U.S. Cl. .................. 128/204.26; 128/204.21; 128/204.23

[58] Field of Search ............... 128/204.21, 204.23, 128/204.26, 204.18

[56] References Cited

U.S. PATENT DOCUMENTS

| | | | |
|---|---|---|---|
| 3,905,362 | 9/1975 | Eyrick et al. | 128/204.18 |
| 3,927,327 | 8/1976 | Ernst et al. | 128/204.21 |
| 3,961,627 | 6/1976 | Ernst et al. | 128/204.21 |
| 4,527,557 | 7/1985 | DeVries et al. | 128/205.24 |
| 4,686,974 | 8/1987 | Sato et al. | 128/204.23 |
| 4,776,333 | 10/1988 | Miyamae | 128/204.21 |
| 4,823,788 | 4/1989 | Smith et al. | 128/205.24 |

OTHER PUBLICATIONS

S. McPherson, Respiratory Therapy Equipment (1985)
Siemens Servo Ventilator 900C Operating Manual.
Veolar Operators Manual (Hamilton Medical) Bird 6400ST Volume Ventilator.
Engstrom Erica Reference Manual Bear 2 Instruction Manual.
Cox, Tinoli and Farrimond, "Investigation of the Spontaneous Mode of Breathing of Different Ventilators", *Intensive Care Med* (1988) 14:532-537.
Dupuis, "Response Time: Flow By vs. Pressure", RRT/Vol. 24/Issue 3/1988.
Kacmarek, "The Role of Pressure Support Ventilation in Reducing Work of Breathing", Respiratory Care, Feb. 1988, vol. 33, No. 2 99-120.
Gurevitch et al., "Importance of Trigger Sensitivity of Ventilator Response Delay in Advanced Chronic Obstructive Pulmonary Disease with Respiratory Failure", *Critical Care Medicine*, vol. 17, No. 4, pp. 354-359.
Katz, et al., "Inspiratory Work and Airway Pressure with Continuous Positive Airway Pressure Delivery Systems", Chest, 88/4 Oct. 1985.
Brouchard et al., "Inspiratory Pressure Support Prevents Diaphragmatic Fatigue during Weaning from Mechanical Ventilation", Am. Rev. Respir. Dis. 1989; 139:513-521.
Dupuis, "Ventilators Theory and Clinical Application", Servo 900C, p. 493-Pressure Support Mode, The C. V. Mosby Co., @1986.

*Primary Examiner*—Edgar S. Burr
*Assistant Examiner*—Kimberly L. Asher
*Attorney, Agent, or Firm*—Fulwider, Patton, Lee & Utecht

[57] ABSTRACT

The system and method for flow triggering pressure supported ventilation include a source of a predetermined, preinspiratory, constant flow of breathing gas to a patient, one or more flow sensors for measuring the rate of gas flow in a flow path communicating with the patient, means for determining when inhalation from the flow path has occurred, and means for generating pressure support in the delivered gas flow in response to inhalation by the patient, means to terminate pressure support when inspiratory phase concludes, and means to reestablish the predetermined, preinspiratory, continuous flow of breathing prior to the patient's next inspiratory effort. A plurality of individual gas sources preferably provide a controlled mixture of breathing gas. In combination with pressure support to the patient during the inspiration effort, the flow triggering strategy of the invention offers significant improvements in providing breath support to patients having weakened respiratory capabilities.

16 Claims, 5 Drawing Sheets

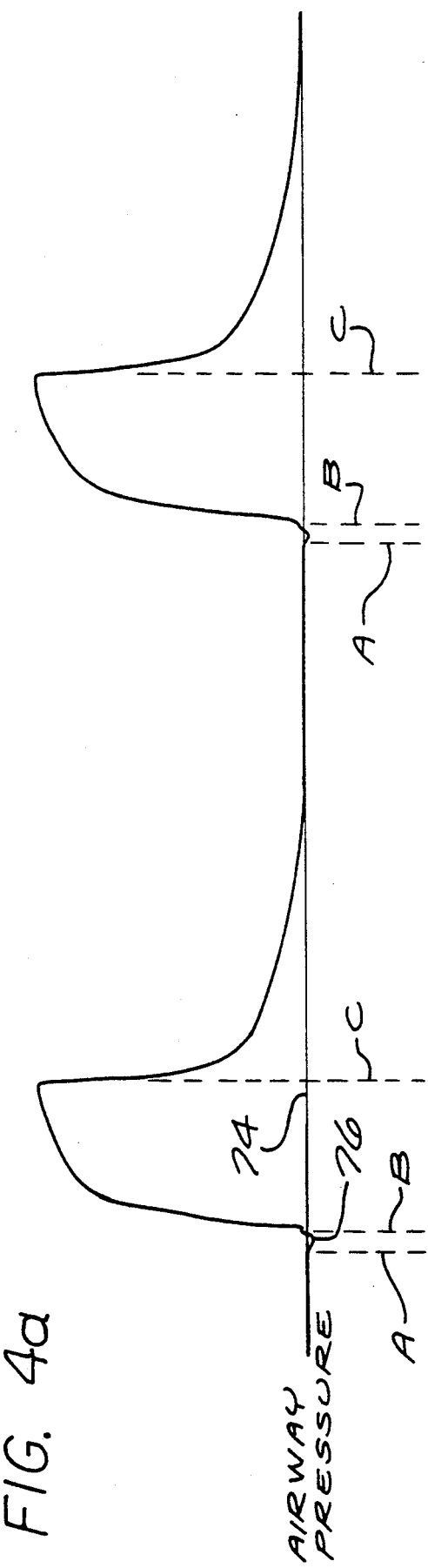
FIG. 4a
FIG. 4b

SYSTEM AND METHOD FOR FLOW TRIGGERING OF PRESSURE SUPPORTED VENTILATION

BACKGROUND OF THE INVENTION

1. Field of the Invention

This invention relates generally to breathing ventilators, and more particularly relates to a pneumatically driven, electronically controlled, ventilator system for providing breathing gas to a patient, and a system and method for flow triggering pressure support during patient-initiated spontaneous breathing. Pressure support is also known in the art by other names, e.g. inspiratory assist, pressure assist, or inspiratory pressure assist.

2. Prior Art

Breathing ventilator systems conventionally provide a breathing gas for either non-pressure supported breaths during inspiration at a pressure level typically no more than 2 cm. of water above or below the pressure baseline or pressure-supported breaths of breathing gas at a support pressure during inspiration as high as 70-100 cm. of water. Such breathing gas is often supplemented with a higher proportion of oxygen than is found in the ambient atmosphere. The respiration work performed by a patient on a ventilator may be divided into two major components: the work to initiate a breath and the work to sustain a breath. It is desirable to reduce the effort expended by the patient in each of these phases, since a high level of such effort can cause further damage to a weakened patient or be beyond the capabilities of small or disabled patients. As discussed below, a variety of strategies and systems have been developed to address these problems, but important issues still remain in the reduction of work demanded by ventilators to command and sustain a breath.

Ventilators presently known in the art are commanded to deliver inspiration support, or a specific flow of breathing gas during an inspiratory phase of breathing, based upon a "pressure trigger" as described below. With such a system, when a patient's spontaneous inspiratory effect withdraws a small volume of gas from the breathing-gas circuit, the corresponding drop in pressure in the closed ventilator circuit is monitored, and when a predetermined triggering pressure threshold is reached, a control mechanism causes the ventilator's pneumatic system to deliver breathing gas at the desired pressure or flow rate. This activation of the ventilator cycle by means of a patient-induced negative pressure may be termed "pressure triggering". A certain amount of lag time and associated negative pressure always occurs between the onset of inspiratory effort and the time that the gas pressure or flow reaches the patient's airway. This lag time (or delay) is generally referred to as a ventilator's response time, and commonly occupies a small but significant portion of a patient's total inspiration time.

Pressure triggering of inspiration support relies upon the transmission of pressure waves throughout the closed breathing-gas circuit. These pressure waves travel to the pressure sensor at the speed of sound in the gas, which is approximately 1 millisecond per foot. Although electronic processing of pressure-wave signals can occur very rapidly, due to factors inherent in ventilator design, patient-inspiration effort can typically continue for as long as 40 to 50 milliseconds without ventilator assistance. Under the conventional pressure-triggering ventilation schemes, the pressure drop, which a patient is required to create in a closed breathing-gas circuit in order to trigger a breath, can require a significant expenditure of energy by the patient. This imposed work on the patient can be detrimental in that respiratory muscles already fatigued by an operation or other patient condition may fatigue. In addition, this respiratory work may be beyond the capability of some patients, such as neonates, small children, or patients severely weakened by trauma or disease, resulting in the inability of the patient to rhythmically trigger the inspiratory support of the ventilator. If this process continues to worsen, the patient may experience failure or severe compromise of the ventilation process. Thus, the ventilator response time, plus the lag time associated with pressure triggering, can result in a significant expenditure of work by the patient in order to command a breath from the ventilator.

The signal to cycle on the ventilator to deliver pressure or volume support of patient breaths by monitoring flow in the patient's breathing-gas circuit or inside the ventilator has recently been accomplished in the context of a closed breathing-gas circuit. In such a system, a single flow sensor is typically positioned inside the ventilator to monitor the flow of gas that a patient withdraws from the closed system and trigger a pressure-or volume-based breath when the patient's inspiratory flow equals a certain predetermined level. However, such a closed-system, flow-based trigger is not an improvement over a closed-system pressure triggered arrangement, because all of the same delays and work required of the patient are present. In addition, a significant negative pressure drop is still required to start the breath, and there is no continuous flow to support the earliest phase of the breath. Therefore, the patient must overcome the substantial inertia of the breath triggering process.

In order to decrease the work of sustaining the flow of a breath after it has been initiated, thereby reducing the work required of our patient, breathing ventilator systems conventionally provide a breathing gas for non-pressure supported breaths during inspiration at a pressure level typically no more than 2 cm. of water above or below the pressure baseline. In pressure-supported systems, breaths of breathing gas are delivered at a pressure support level during inspiration as high as 70-100 cm. of water. These higher pressures are used to supplement patient effort, overcome airway resistance, and reduce the work of breathing for the patient. This use of a higher pressure support level can provide enhanced comfort for the patient, and may facilitate the weaning of the patient from the ventilator.

To circumvent or overcome the problems associated with breath triggering in the context of a closed ventilator circuit, a continuous flow system may be employed. To ensure that the patient receives a flow of breathing gas immediately upon initiation of an inspiratory effort and with the appropriate oxygen concentration, a flow regulator is positioned at the inlet of the breathing-gas circuit to deliver a constant gas flow in excess of the peak-flow demand expected from the patient. This "continuous flow" approach eliminates the ventilator's delay time and significantly reduces the negative pressure work associated with closed ventilator systems.

An advantage of the continuous gas flow (available in an open breathing-gas system) is that a patient's inspiratory effort results in an immediate flow of breathing gas into his/her trachea, without the delays and with less negative pressure work inherent in closed ventilator systems. Thus, it would be desirable to provide pressure support to a patent in an initially, open continuous-flow system rather than from a closed breathing gas system. It would also be desirable to provide a method and system for triggering breaths which can be made to be more sensitive than previous pressure-based strategies.

From the above, it is clear that it would be desirable to combine the advantages of flow sensing and triggering in a functionally open, breathing-gas circuit with pressure support for the purpose of enabling the ventilator to reduce significantly both the work of breathing during the earliest phase as well as the patient's breathing work during the later phases of the inspiratory effort. The present invention accomplishes these goals.

SUMMARY OF THE INVENTION

An excessively high expenditure of energy by the patient, early in the inspiratory process, can be detrimental to the patient. Patients may fatigue under these imposed workloads, leading to further respiratory distress and/or failure. The required energy expenditure can also create difficulties in weaning the patient from the ventilator, leading to patients who become ventilator dependent. Thus, reducing the energy expenditure while breathing on a mechanical ventilator is advantageous for the patient.

The energy expended while breathing on a mechanical ventilator may be divided into two components. The first of such components is the energy required to trigger the ventilator to initiate inspiratory support. The second component is the energy required to maintain gas flow once the inspiration has been initiated. The use of flow triggering within the context of a continuous gas flow system minimizes the first component, since a patient has a continuous supply of appropriately mixed gas immediately available from which to draw, essentially eliminating the lag time and minimizing the earliest work of breathing for volume- or pressure-based, patient-initiated breaths. The strategy behind the pressure support mode of ventilation is to reduce the second component by providing a positive pressure to overcome airway resistance and to supplement patient effort. While each of these techniques is helpful in reducing the work to be performed by the patient on the respirator, it would be desirable to provide a ventilator system that combined these two work-reducing concepts, thereby enabling the ventilator to manage all phases of the energy expended by the patient. Such a level of performance is unavailable in current systems.

The present invention provides a system and method of triggering pressure supported breaths for a patient on a ventilation system that is initially open (and is provided with a pre-inspiratory flow of breathing gas) and that is equipped to measure the flow of inhaled gas into the patient and then triggers the delivery of pressure support when the flow of inhaled gas equals a preset, threshold value of flow. By implementing flow sensing in an open-circuit design, in which setting the ventilator establishes a controlled and minimal, pre-inspiratory, continuous flow of gas in the breathing-gas circuit, the ventilator acquires the means to cycle on the pressure support function while eliminating the ventilator's lag time and minimizing the patient's earliest inspiratory efforts. When this method of flow triggering is combined with pressure support ventilation, the patient's work of breathing can be managed to virtually any desirable level. An additional benefit provided by flow triggering of pressure supported ventilation is the elimination of self-triggering of the ventilator due to leaks in the patient's physiology and/or the breathing-gas circuit, without degrading ventilator sensitivity. The system of the present invention also allows the measurement of these leaks, which can then be used to assess the condition of physiologic leaks in the patient.

Briefly and in general terms, the flow triggering system for delivering breathing gas to a patient of the present invention comprises a source means of a pre-inspiratory, constant flow of breathing gas to a patient, flow sensor means for measuring the rate of gas flow in a flow path means communicating with the patient, a means for determining when inhalation from said flow path has occurred, a means for generating pressure support during the inspiratory phase of the breath in response to inhalation by the patient, and a means for reestablishing the constant flow of breathing gas to a patient after the end of the inspiratory phase of the pressure supported breath and before the new inspiratory effort begins.

In the preferred embodiment of the system of the invention, a plurality of individual gas sources provides a controlled mixture of breathing gas. It is preferable to mount flow sensor means in both the flow path to (inspiration) and the flow path from (exhalation) the patient, and measure the flow extracted by the patient as the difference of the two. It is preferred to discontinue pressure support at the conclusion of the inspiratory phase of the breath. And it is also preferred to reestablish the continuing flow of breathing prior to the patient's next inspiratory effort.

In the preferred method of the invention, the flow triggering of pressure supported ventilation involves the steps of (1) providing a predetermined, pre-inspiratory, continuous flow rate of breathing gas from a source to the patient, (2) measuring the flow rate in the ventilation flow path, due to the patient's inhalation as the difference between flow rates measured by flow sensor means placed in the paths to and from the patient, (3) generating pressure support during the inspiratory phase of the breath when the flow due to inhalation exceeds a predetermined threshold value, and (4) reestablishing the predetermined, continuous flow rate of breathing gas from a source to the patient prior to his/her next respiratory effort. The method further preferably comprises mixing a plurality of individual gases from different sources, and controlling proportions of the mix of gases. It is currently preferred to discontinue pressure support when an exhalation effort is detected from a rise in pressure to a threshold value, or when flow declines to below a threshold value.

The approach of the present invention to the combination of flow triggering with pressure support provides a spontaneous breath whose work of inspiration can be closely controlled by an appropriate selection of the level of support pressure. The energy required to trigger the breath is minimal due to the flow triggering strategy described in the invention. Once the breath is triggered, the level of support pressure in combination with the patient's airway resistance (including that of the artificial airway and lumped chest well and lung compliance) allows the energy expended throughout the rest of the inspiratory phase to be closely managed. There are also other advantages to flow triggering of pressure-supported ventilation when used for small children or infants, where the high sensitivity of triggering is a distinct advantage, since small patients find pressure triggering more strenuous due to their weaker respiratory systems. In addition, the dead space that must be evacuated for pressure triggering is also more difficult for patients with small lungs. Very often, patients who cannot successfully pressure trigger a ventilator can flow trigger the ventilation process.

These additional advantages of the present invention derive in part from the physics of the flow-triggering strategy Before a patient initiates an inspiratory effort, a predetermined, preinspiratory controlled, and measured flow of breathing gas is delivered into the patient's breathing-gas circuit. This breathing gas (air or oxygen-enriched air) flows past the patient wye, which is connected to the patient's breathing attachment (artificial airway, face mask, nasal mask, or the like), and then flows out of the breathing-gas circuit, where it is measured by the flow-sensing means placed in this flow path. Functionally, the patient's breathing attachment is connected, via the patient's wye, to an artificial atmosphere (either at or above the ambient atmospheric pressure), the oxygen concentration of which is determined by the setting from the plurality of gas sources. From the patient's reference point, the breathing-gas circuit is not closed as it is for the pressure triggering strategy, but open as provided for by the preinspiratory continuous flow of breathing gas. At the moment that the patient initiates an inspiratory effort and immediately thereafter, the flow past the patient wye will exceed the flow through his or her breathing attachment. Thus, in the flow triggering system, breathing gas flows with no delay into the patient's breathing attachment the moment that the inspiratory effort begins. In contrast, in the pressure triggering system flow through the patient's breathing attachment from the ventilator is delayed until the pressure threshold is attained and the ventilator senses this event, thereafter causing the flow source means to deliver flow into the breathing-gas circuit.

The flow-triggering method of the present invention may be implemented in the following preferred embodiment: The predetermined preinspiratory flow of gas that enters the breathing-gas circuit from the flow source means is preferably greater than the magnitude of the flow through the patient's breathing attachment, which is the actual threshold flow signal that causes the ventilator to cycle on and deliver the pressure-supported breath. Preferably, the predetermined flow into the breathing-gas circuit should exceed the value of the flow which results from the patient's inspiratory effort and which triggers the ventilator cycle on and deliver the pressure-supported breath. With this design, the patient's breathing-gas circuit functions as an open continuous flow system until and after the patient's inspiratory effort generates the flow-triggering signal.

A benefit of the present invention is that the pressure in the breathing circuit during the early exhalation phase may be kept low to limit the problems encountered when the patient tries to exhale against an artificially high back pressure due to high continuous flow. This feature improves the ability of the respirator to reduce the work of exhalation and still provide an elevated pressure in the patient's airway to allow the practitioner to manage the work of initiating a breath and supporting the early phases of the breath.

Another benefit of the present invention is its ability to more efficiently deal with leaks in the patient and ventilator system. Leaks are a problem often encountered in pressure triggered ventilation systems. Leaks in the patient and ventilator system are quite common, making it difficult to maintain pressure in the breathing-gas circuit. These leaks may be external to the patient, such as those in the tubing connections from the ventilator to the patient, or internal, such as those leaks in the patient physiology. Leaks with pediatric patients are common due to the use of uncuffed endotracheal tubes, which do not form a tight seal with the patient's airway. Whatever the source, the leak can cause false pressure triggering of breaths, as the drop in pressure is interpreted as a patient inspiratory effort. To prevent false pressure triggering, sensitivity may be reduced, unfortunately making pressure triggering even more difficult for a patient once the leak has been eliminated (e.g., the closing of a physiologic leak). On the other hand, leaks encountered during flow triggering can be corrected without impairment of sensitivity because precise control of flow is an inherent component of the flow-triggering strategy. In addition, changes in the flow-trigger level do not affect sensitivity to the same extent as do changes to the pressure-trigger level. In patients with physiologic leaks, the flow-triggering system may be used to assess the magnitude of these leaks. By titrating the flow-trigger level until the ventilator self cycles, one can measure the physiologic leaks as well as system leaks. This technique can be used to monitor the opening or closing of these physiologic leaks throughout the patient's ventilator care.

From the above, it will be evident to those skilled in the art that flow triggering of pressure supported patient breaths from a continuous flow system provides important advantages over previous patient ventilation systems. Other aspects and advantages of the invention will become apparent from the following detailed description and the accompanying drawings, which illustrate by way of example the features of the invention.

BRIEF DESCRIPTION OF THE DRAWINGS

FIG. 4a shows a graph of pressure measurements over time for a typical flow-triggered, pressure-supported breath.

FIG. 4b shows as graph of flow measurements over time for a typical flow-triggered, pressure-supported breath.

DETAILED DESCRIPTION OF THE PREFERRED EMBODIMENTS

Figure 1:
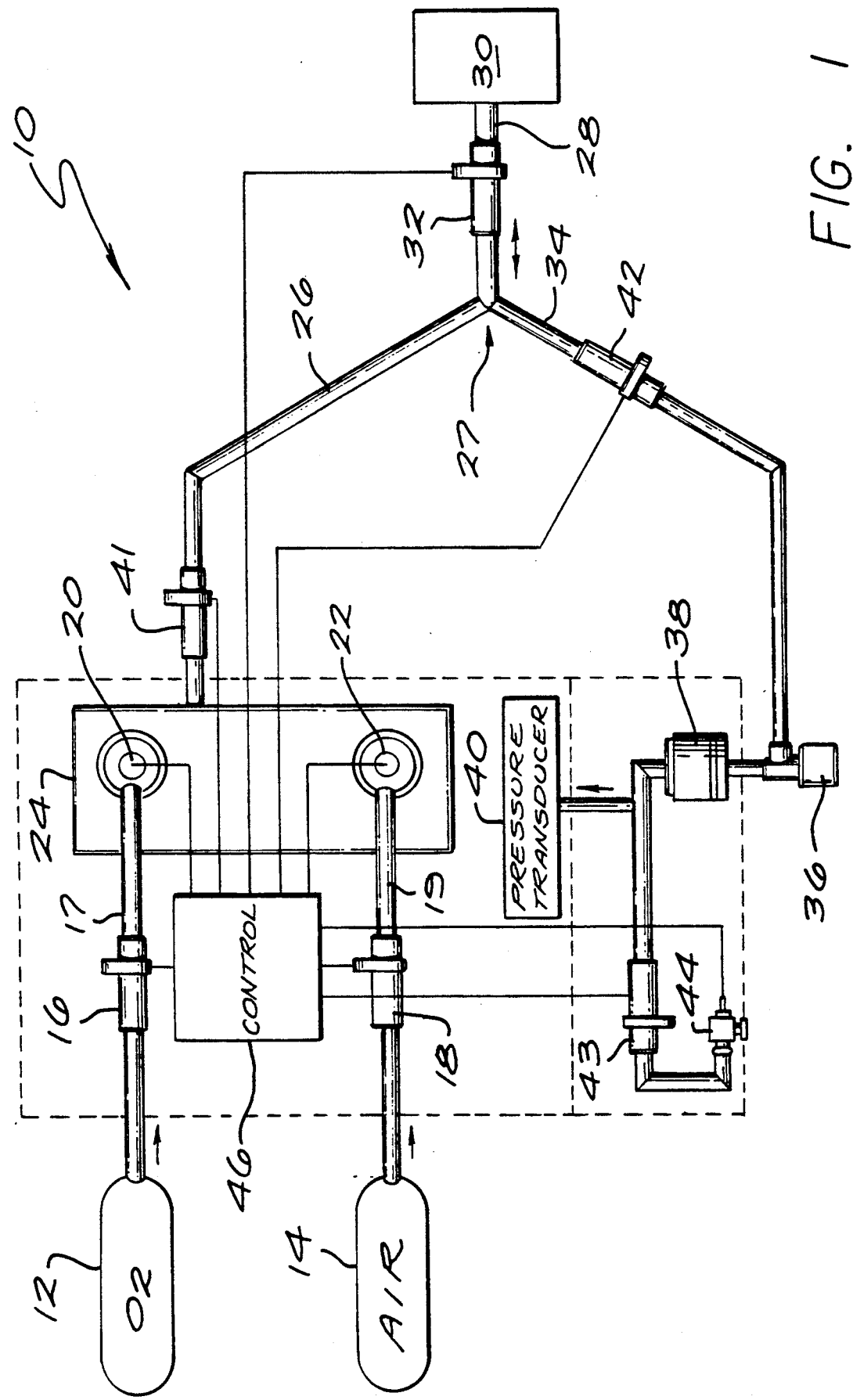
FIG. 1 is a schematic diagram of a flow-triggered, open circuit ventilation system.

As is shown in the drawings, which are included for purposes of illustration and not by way of limitation, the invention is embodied in a system for flow triggering a pressure-supported ventilation system which reduces the patient work of breathing, provides improved triggering of the pressure supported breath and allows improved management of the pressure support during a breath. The flow-triggering system is used in patient ventilation systems having a source of breathing gas for a patient, a flow-path communicating with the patient, and flow-sensor means for measuring the gas flow to and from the patient. The breathing-gas source provides a predetermined, preinspiratory, continuous rate of flow of breathing gas to the patient and the flow-sensors measure the rate of gas flow to and from the patient. The system determines the difference between the measured flow rate from the patient and the predetermined rate of delivered gas flow to the patient. The system then generates pressure support in the delivered flow of gas when the difference between the flows to and from the patient equals a predetermined threshold or trigger value. The breathing gas may be enriched with a higher concentration of oxygen than normal air. The source of breathing gas may include more than one individual gas source and may also include a device for mixing and controlling the proportions of the individual gases. The system also preferably includes means for determining when exhalation occurs, so that pressure support may be discontinued until it is again triggered.

In accordance with the present invention, there is provided a method for flow triggering of pressure-supported ventilation in open ventilation system having a source means of breathing gas, a flow-path means for the breathing gas in fluid communication with a patient, and flow-sensor means for measuring the rates of gas flow in the flow path. The method comprises delivering a predetermined, continuous rate of flow of the breathing gas from the breathing gas source to the patient prior to breath initiation; measuring the rates of gas flow in the ventilation flow path due to inhalation; generating pressure support in the delivered flow of gas when the rate of gas flow due to inhalation equals a predetermined threshold value; termination of the pressure-supported breath when the patient initiates an expiratory effort, or when flow in to his or her breathing attachment declines to a predetermined level; and means to reestablish the predetermined continuous rate of flow of the breathing gas from the source to the patient prior to initiation of the next breath.

The present invention also provides for a system for flow triggering of pressure-supported ventilation for use in a functionally open ventilation system having a source means of breathing gas, a flow path means for the breathing gas in fluid communication with a patient, and flow sensor means for measuring the rate of gas flow in the flow path. The system includes means for delivering a predetermined, preinspiratory, continuous rate of flow of the breathing gas from the source to the patient; means for measuring the gas flow in the flow path due to inhalation; means for generating pressure support in the delivered flow of gas when the gas flow due to inhalation equals a predetermined threshold value; means for terminating the pressure-supported breath when the patient initiates an expiratory effort or when flow into his or her breathing attachment declines to a predetermined level; and means to reestablish the predetermined, preinspiratory, continuous rate of flow of breathing gas during the exhalation interval.

FIG. 1 is a schematic of a present system for flow triggering ventilation according to the present invention. In the currently preferred embodiment, the system 10 includes a source of oxygen gas ($O_2$) 12, which is typically a pressurized tank of oxygen, and a source of air 14, which may also consist of a high-pressure tank of air. The sources of air 14 and oxygen 12 may also typically include pressure regulators. The air supply source may also comprise an air compressor which supplies air taken from the ambient atmosphere. Other conventional sources of pressurized oxygen and air in hospital or patient-care settings would also be appropriate.

The source of oxygen is connected to a flow meter 16 in the oxygen line 17, and a similar flow meter 18 for the air source 14 is provided in the air line 19. The oxygen line 17 delivers oxygen to its proportional solenoid valve 20, and the air line 19 similarly delivers air to its proportional solenoid valve 22, the two valves releasing oxygen and air for mixing in the mixing chamber 24. Valves other than proportional solenoid valves and mixing means other than mixing chamber 24 may also be appropriate. The mixed gas is delivered from mixing chamber 24 through the airway conduit 26 to the patient wye fitting 27, which is connected to the patient breathing attachment 30 by breathing tube 28. The breathing attachment 30 may be simplified or replaced by other breathing means in certain implementations. In these implementations the breathing-gas flow may be delivered to the patient by means of a breathing tube (artificial airway) or by a breathing mask or other means for delivering breathing gas to the patient's trachea. In either implementation and prior to and immediately after the inspiratory flow, flow meters 16 and 18 monitor the flow of gas to the patient during the continuous flow of gas from the oxygen and air sources (up to and including the time at which the patient's inspiratory flow equals the triggering threshold flow signal) and during exhalation. Exhalation gas from the patient area flows through the exhalation conduit 34 and exhalation flow meter 43. The difference between the sum of flow meters 16 and 18, and exhalation flow meter 43 provides a measurement of flow of breathing air inhaled by the patient from the continuous flow of breathing gas delivered to the patient from the oxygen and air source means. To assist control of the delivery of breathing gas to the patient, the flow-control algorithm may monitor flow sensors 16, 18, and 43. During operation of the flow-triggering phase and for the restoration of the preinspiratory, continuous flow during exhalation and prior to the patient's next inspiration, flow sensors 16, 18, and 43 become primary inputs to the flow-control algorithm prior to the initiation of the inspiratory effort, immediately after the inspiratory effort, and during exhalation when the preinspiratory, continuous flow is being reestablished.

Beginning with and immediately after the patient's inspiratory effort, the flow of breathing gas to the patient will exceed the flow of breathing gas from the patient, and the difference between the flow to and from the patient is compared with a predetermined, "flow-trigger" threshold level. This measurement of flow inhaled by the patient is used for triggering the initiation of pressure-supported inspiration. In a preferred embodiment, prior to return of the exiting or exhalation gases to the ambient atmosphere, said gases are passed through a fluid collector vial 36 and a heated bacteria filter 38 provided in the exhalation conduit line. A pressure transducer 40 for measuring the pressure during both inspiration and exhalation may also be provided in the exhalation conduit 34. The system may also include an exhalation valve 44 to close the system to allow breaths and to open the system for exhalation to the atmosphere, to thereby return the filtered and cleaned exiting gas to the atmosphere from the open ventilator system.

The invention may use other methods for measuring the inhaled flow by the patient from the preinspiratory, continuous flow of breathing gas. A flow meter 32 may be placed between the patient wye 27 and the patient attachment 30 to measure patient inhalation flow directly. Alternatively, or in addition to flow meter 32, a delivery flow meter 41 may be provided in the airway conduit 26 for measuring the flow of mixed breathing gas delivered to the patient, and an exhalation flow meter 42 may be installed in the exiting airway conduit 34 for monitoring the flow of gas from the patient during inspiration effort and exhalation. The difference between flow meters 41 and 42 also provides a measurement of flow inhaled by the patient from the preinspiratory, continuous flow of breathing gas from the source means.

It will be understood by those skilled in the art that any combination of signals from flow meters 16, 18, 32, 41, 42, and 43 may be used for sensing and measuring the flow inhaled by the patient for use as a flow-trigger signal for inspiration.

An electronic control means 46, preferably including a microprocessor for controlling all of the functions of the ventilator control system, is connected to the oxygen-source flow meter 16, the air source flow meter 18, the oxygen proportional solenoid valve 20, the air proportional solenoid valve 22, the patient exhalation flow meter 43, and any additional flow meters (41) in the inspirational airway conduit 26, the patient wye flow meter 32, or flow meters (42) in the exiting or exhalation airway conduit 34. Electronic control means 46 compares the rate of flow to the patent through the patient wye 27 as derived by any of the previously discussed means, with a predetermined flow threshold level to detect whether the patient's inspiratory effort has met the criterion for triggering pressure support by operation of the proportional solenoid valves 20, 22. The control means 46 also controls the proportional mixing through the proportional solenoid valves 20, 22, and operates to open the exhalation valve 44 and cause the proportional solenoid valves 20, 22 to discontinue pressure support when the exhalation effort of the patient is detected, returning the flow of breathing gas to the patient to the preinspiratory level of continuous flow in readiness for the patient's next inspiratory effort.

The flow triggering of breaths involves monitoring the flow of inhaled gas from the continuous flow of breathing gas delivered to the patient, which reduces the energy required from the patient to initiate a ventilator breath, and turning on the inspiratory pressure support when the patient's inspiratory flow meets the triggering criterion. The continuous, minimal flow of breathing gas delivered into the breathing circuit prior to the initiation of the inspiratory effort serves two functions: First, the continuous flow converts the normally closed breathing-gas circuit into one that is functionally open. Second, the continuous flow establishes a highly stable flow of breathing gas which can be monitored by the flow sensing means to determine when the patient begins his or her inspiratory effort. This flow triggering approach converts the initial work of inspiration from an essentially isometric effort to a quasi-isotonic effort. Both the level of continuous flow and the required change in flow due to inhalation for inspiratory support triggering may be adjusted through the control means.

As previously discussed, the energy expended by a patient while breathing on a mechanical ventilator can be divided into two components. The first component is the energy required to trigger the ventilator to begin the inspiration. The second component is the energy required to maintain adequate gas flow once the ventilator has been triggered to deliver inspiratory support.

A primary purpose of the pressure support mode of ventilation is to reduce the second energy component. This is accomplished by providing a positive pressure level during the inspiratory phase of the breath. This positive pressure may be used to reduce or negate the imposed work due to the resistance of the artificial airway, and/or the resistance and compliance intrinsic to the patient's respiratory system. In extremely weak patients, the application of pressure support can provide sufficient tidal volumes without using assist-control ventilation, and can thereby increase patient comfort while returning to the patient some measure of control over his or her breathing pattern. Patients have been shown to expend less work or energy in breathing when pressure support is used. This can have important implications when weaning patients from the ventilator, since the patient must then be progressively strengthened to breath without the pressure support to inspiration.

Figure 2A:
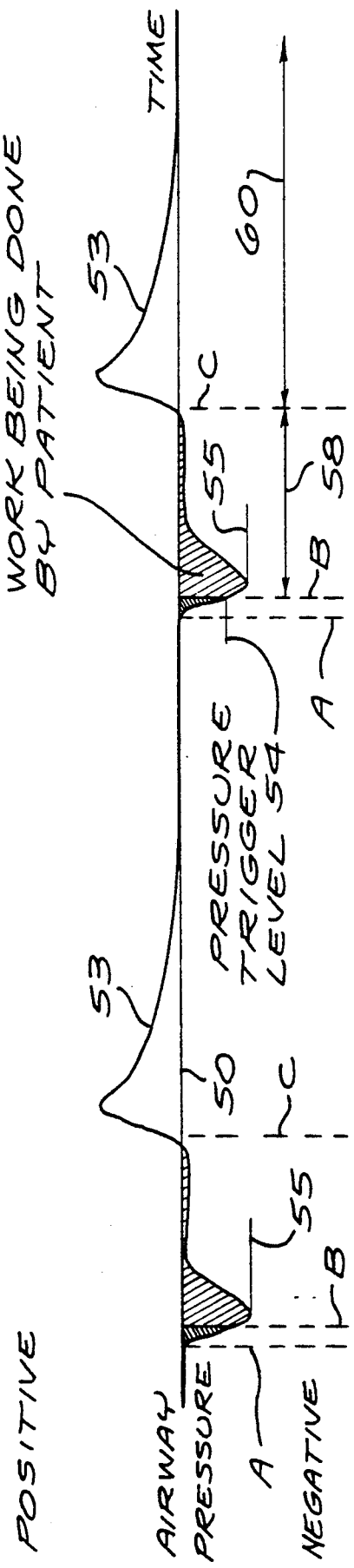
FIG. 2a shows a graph of pressure measurements over time for a typical pressure-triggered breath without pressure support.
Figure 2B:
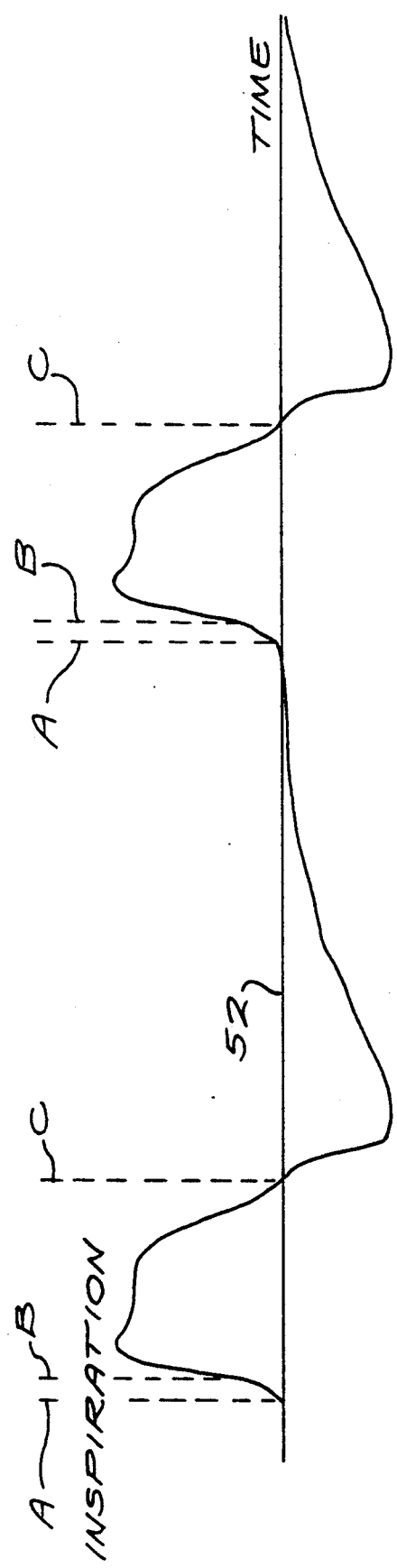
FIG. 2b shows a graph of flow measurements over time for a typical pressure-triggered breath without pressure support.

FIGS. 2a and 2b show traces of pressure over time and flow over time, respectively, as they vary from the patient pressure baseline 50 (FIG. 2a) and the patient flow baseline 52 (FIG. 2b) for a typical spontaneous, non-pressure supported, ventilator-delivered breath. In FIG. 2a, the area under pressure-time trace 53 which is below the pressure baseline 50 represents the work being done by the patient. The portion of the curve 53 in the pressure-time trace between point A and point B at the pressure trigger level 54 depicts the portion of this work required to trigger inspiratory support. The portion of the curve between points B and C represents the remaining work of inhalation 58 required to maintain an adequate gas flow to satisfy the inspiratory demands of the patient. In other terms, the area between B and C represents the work required of the patient to sustain the breath. Note (with respect to the pressure baseline 50) that, as shown in FIG. 2a, the pressure is negative throughout inspiration, indicating that the patient is performing work during this entire period. It should also be noted that the peak negative pressure required of the patient is the level 55 noted on FIG. 2a. The exhalation phase 60 begins at the end of the inhalation phase. FIG. 2b shows the flow rates corresponding to the pressure-time curves of FIG. 2a. It is evident that the flow prior to B, the point at which the pressure triggering is effecting is very low and that substantial work is still performed by the patient between B and C, even though the pneumatic system was cycled on at B.

Figures 3A, 3B:
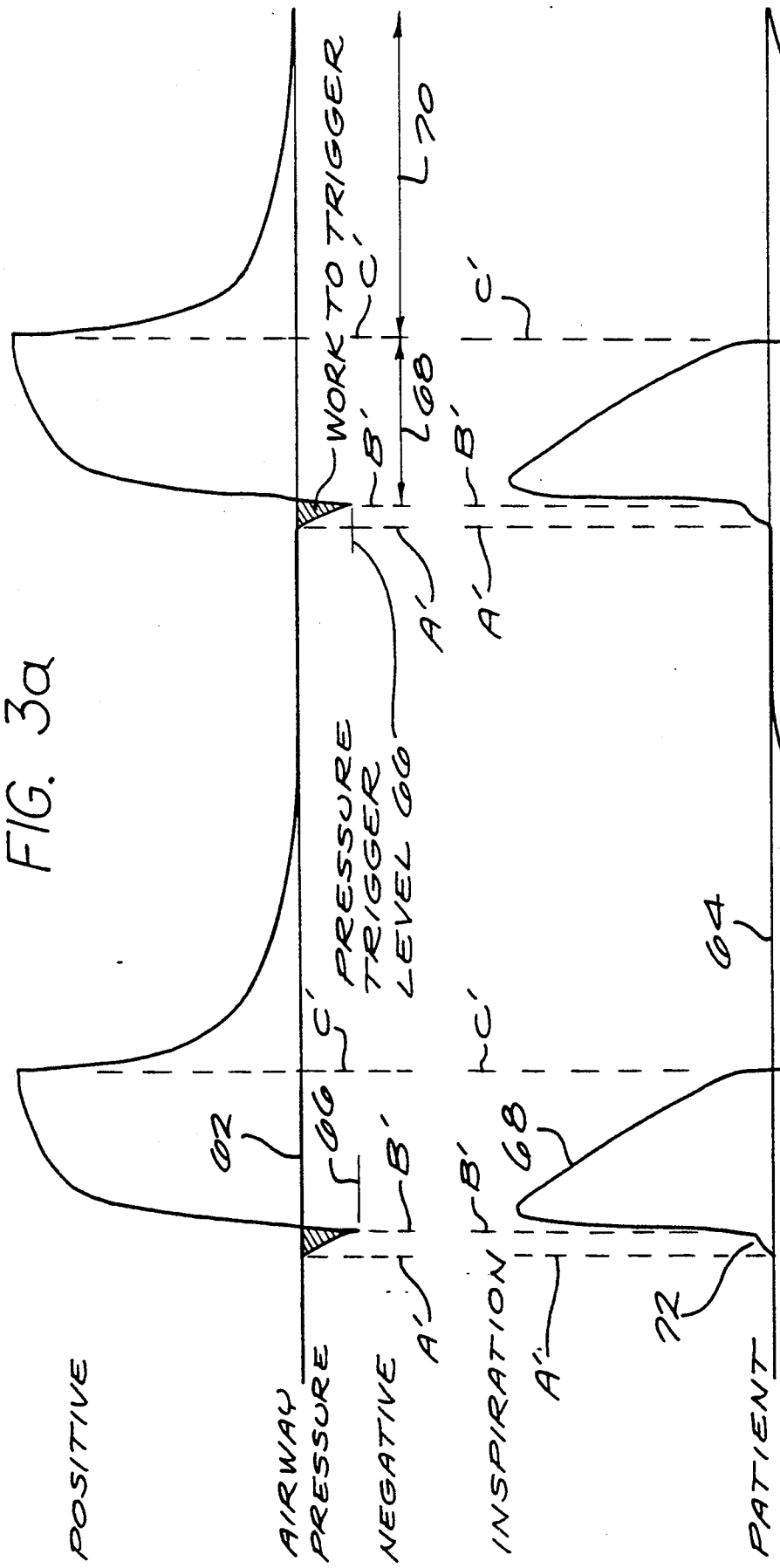
FIG. 3a shows a graph of pressure measurements over time for a typical pressure-triggered, pressure-supported breath.
FIG. 3b shows a graph of flow measurements over time for a typical pressure-triggered, pressure-supported breath.

FIGS. 3a and 3b show traces of pressure over time about a patient pressure baseline 62, and flow over time about a flow baseline 64, respectively, for a typical pressure-triggered, pressure-supported breath. Once the breath is triggered at B representing the pressure trigger level 66, the ventilator creates a positive pressure to reduce the patient's work of inspiration. Prior to the inspiration cycle 68, a negative pressure, and therefore an expenditure of energy by the patient, is required to trigger the breath. Pressure support is discontinued when the patient exerts an expiratory effort or when flow into his/her lungs declines to a preselected value. At this point, the patient begins the exhalation phase 70. It may be seen that the flow level at the time of triggering 72 was relatively low, but rapidly increased in response to the pressure support supplied after pressure triggering. However, there remains a substantial amount of work which must be expended by the patient for this scheme as well.

As illustrated in FIGS. 4a and 4b, the present invention's combination of flow triggering with pressure support (with an appropriate selection of the support pressure) can reduce the energy expenditure by the patient to a virtually negligible level.

FIGS. 4a and 4b show traces of pressure over time about a patient pressure baseline 74, and flow over time about a flow baseline 78, respectively, for a typical, flow-triggered, pressure-supported breath according to one embodiment of the present invention. Comparison of FIGS. 3a and 4a shows that the pressure 66 required for pressure triggering is more negative compared with the pressure 76 resulting from flow triggering. The negative pressure component 66 (in the pressure-triggering example of FIG. 3), representing the work done by the patient, is substantial, whereas the negative component 76 (with flow-triggering example, FIG. 4) is minor. The flow 80 to the patient can be seen to be higher at the flow trigger level in the flow triggered system of FIG. 4b than the flow level 72 in the pressure triggered system of FIG. 3b. With respect to the flow-triggering traces in FIG. 4, both the less negative triggering pressure and the higher inspiratory flows early in the breath, compared to the pressure-triggered traces of FIG. 3 result from the physical differences between the flow systems. In the flow-triggered case, the patient inhales from a functionally open system (i.e., the patient's earliest flow demands are met by the preinspiratory, continuous flow), whereas in the pressure-triggered case, the patient inhales from a closed system (i.e., the patient receives no flow until the pressure-trigger threshold is reached). Thus, it can be seen that the combination of flow triggering with pressure support of the present invention reduces the energy expended by the patient to trigger inspiratory support and also reduces the patient energy required to maintain the inspiratory phase. Thus, by combining flow triggering with pressure support according to the present invention, the work done by the patient to trigger pressure-supported breathing is minimized while the appropriate selection of the support pressure allows the patient's inspiratory work to be set at a desired level. From the above, it may be seen that the work associated with the interval A-B in FIGS. 2 and 3 may be substantially reduced with the present invention as illustrated by the interval A-B of FIG. 4. Thus, while the patient work of FIG. 3 is lower than that of FIG. 2, representing the difference between pressure triggering of flow support and pressure triggering of pressure support, the latter representing a more aggressive technique for support to a pressure triggered system. The present invention further minimizes the patient work compared to these previous strategies.

While pressure support of ventilation has a number of advantages as discussed above, the attendant high pressures in the exhalation limb of the patient's breathing-gas circuit during the exhalation phase of the flow triggered pressure supported breath can be a cause of concern for the patient unless they are carefully controlled. Pressures above the PEEP (baseline pressure value) generally indicate that the patient's lungs are hyperinflated. These events can place the patient's diaphragm and accessory inspiratory muscles in a position of relative inefficiency and may impose a higher work of breathing on the patient. If the patient is alert, he/she may also attempt to forcefully exhale to PEEP (baseline pressure value), which also adds extra work to the breathing effort. Thus it would be desirable to maintain the lowest possible pressures in the patient breathing circuit during exhalation. A long-recognized disadvantage of the earlier developed, continuous flow concept was the presence, in the exhalation limb of the patient's breathing-gas circuit, of the practitioner-selected, continuous flow in addition to the patient's own exhalation flow. This constant extra flow elevated the pressure in the patient's breathing-gas circuit (during exhalation), which could also lead to problems similar to those discussed above.

The present invention of flow triggering can be configured to minimize this extra, non-patient generated exhalation flow in the patient's breathing-gas circuit. According to a preferred embodiment of the invention, when the ventilator declares exhalation and (opens the exhalation valve) the pre-inspiratory, continuous flow of breathing gas is set to a minimal value. This minimal value is maintained throughout the most active phase of the patient's exhalation, then it is reset by the ventilator to the specified value for the pre-inspiratory, continuous flow of breathing-gas, in anticipation of the next inspiratory effort.

Figure 5A:
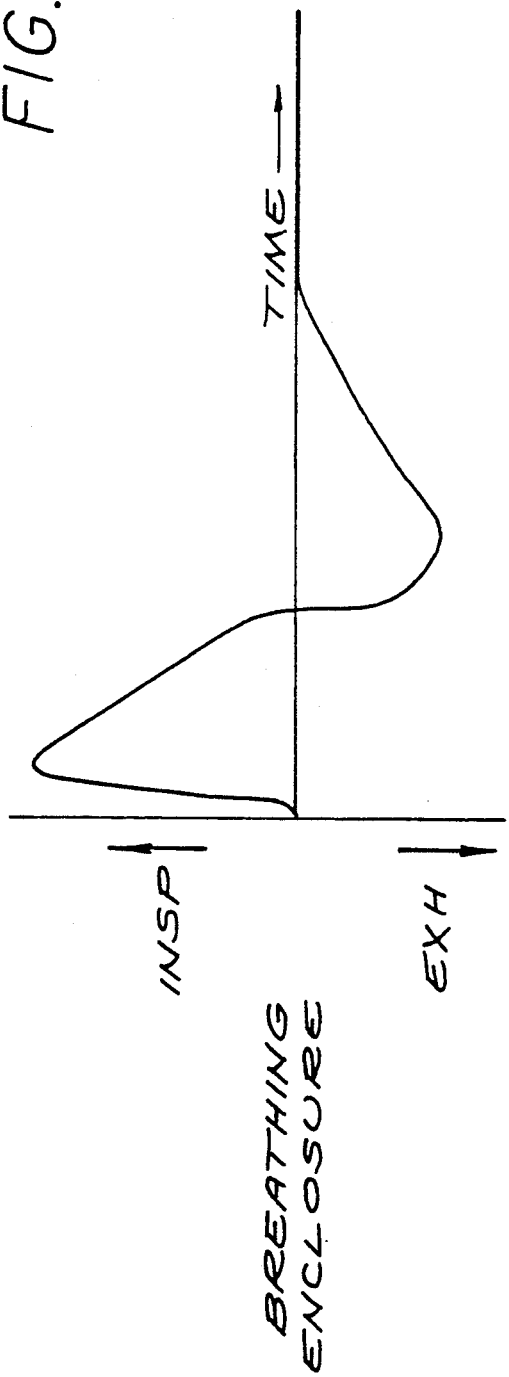
FIG. 5a is an illustration of the patient flow during a single patient breath in a conventional system.
Figure 5B:
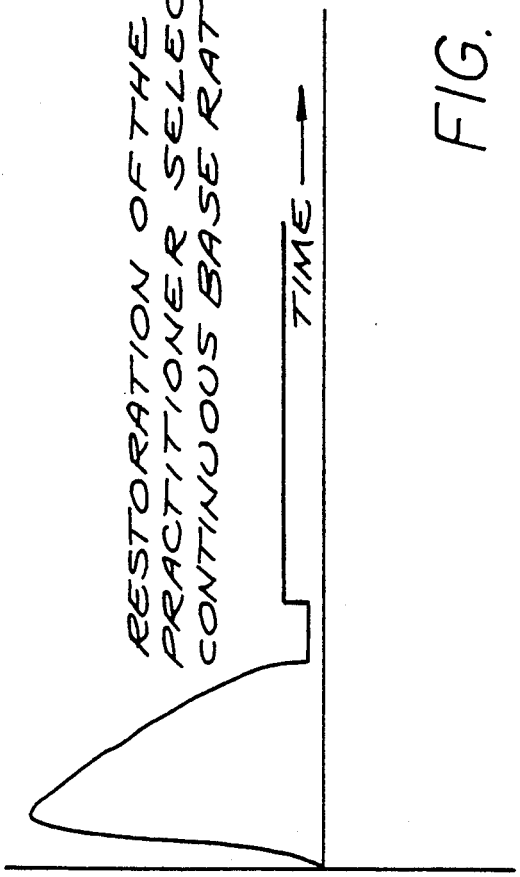
FIG. 5b is an illustration of the flow delivered by the ventilator using the exhalation-flow reduction scheme of the present invention.

FIG. 5 illustrates the function of this preferred embodiment. FIG. 5a illustrates the patient flow above and below baseline in a system of pressure supported breathes as previously described. FIG. 5b illustrates the flow support time history delivered by this preferred embodiment, in which the flow is reduced during the early exhalation period and then returned to the practitioner-selected continuous base flow. By using this scheme, the over-pressurization of the patient's airway is avoided during the early period exhalation, thus reducing the work performed by the patient and limiting the undesirable effects described above.

It may be seen from the foregoing description that the system and method of the present invention allow for reduction of patient discomfort and work of ventilator supported breathing by maintenance of a preinspiratory, continuous flow of breathing gas to the patient and by flow triggering of inspiratory support. In combination with pressure support to the patient during the inspiration effort, the flow triggering strategy of the invention offers significant improvements in providing breath support to patients having weakened respiratory capabilities.

Although a specific embodiment of the invention has been described and illustrated, it is clear that it is susceptible to numerous modifications and embodiments within the ability of those skilled in the art and without the exercise of the inventive faculty. Thus, it should be understood that various changes in form, detail and application of the present invention may be made without departing from the spirit and scope of this invention.

We claim:

1. A method of triggering pressure supported ventilation to a patient supplied with breathing gas from a ventilation system having a source of breathing gas, a patient breathing attachment, an exhalation valve, and a functionally open ventilation flow path in fluid communication with said source of breathing gas, said patient breathing attachment, and said exhalation valve, said ventilation flow path including flow sensor means for measuring flow rate of said breathing gas from said source of breathing gas to said patient and for measuring flow rate of said breathing gas from said patient breathing attachment to said exhalation valve, the steps of the method comprising:

setting a predetermined threshold value;

setting a preinspiratory, predetermined continuous rate of flow;

delivering breathing gas from said source to said patient breathing attachment at said preinspiratory, predetermined continuous rate of flow;

measuring said flow rate of breathing gas from said source of breathing gas to said patient breathing attachment to determine a gas supply flow rate;

measuring said flow rate of breathing gas from said patient breathing attachment to said exhalation valve to determine an exiting gas flow rate;

determining patient inspiratory effort in said flow path by a) comparing said gas supply flow rate with said exiting gas flow rate and b) determining a flow rate difference due to inhalation, thereby indicating the patient's inspiratory effort;

generating pressure support in said breathing gas delivered from said source to said patient when said flow rate difference due to inhalation exceeds said predetermined threshold value;

determining the beginning of the patient's exhalation cycle;

reducing the gas supply flow rate for a predetermined period of time at the beginning of said exhalation cycle; and restoring delivery of said breathing gas from said source to said patient breathing attachment at said preinspiratory, predetermined continuous rate of flow before a next patient inspiratory effort.

2. The method of claim 1, wherein said source of breathing gas comprises a plurality of different gas sources, and further comprises the step of mixing said plurality of different gases.

3. The method of claim 2, further comprising the step of controlling the mixing of said different gas sources according to a predetermined proportion of said different gases.

4. The method of claim 1, wherein said ventilation flow path includes an inhalation and exhalation flow path into and from said patient breathing attachment, and said inhalation flow path and said exhalation flow path form a wye junction communicating with the patient breathing attachment, and the step of determining the rate of gas flow in said flow path comprises measuring gas flow at the portion of the patient wye junction communicating with the patient breathing attachment.

5. The method of claim 1, wherein said flow path includes an exhalation flow path from said patient breathing attachment and an inhalation flow path to the patient breathing attachment, and said step of determining the rate of gas flow into and from said patient breathing attachment comprises performing measurements at least one position in the inhalation flow path and at least one position in the exhalation flow path.

6. The method of claim 1, wherein said flow path includes an exhalation flow path from said patient breathing attachment, and said measurement of said change in the rate of gas flow in said flow path is measured in at least one location in said exhalation flow path.

7. The method of claim 1, further including the step of discontinuing said pressure support when the flow rate in said flow path drops below a predetermined value.

8. The method of claim 1, further including the step of discontinuing said pressure support when the pressure in said flow path rises above a threshold value.

9. The method of claim 1, wherein said ventilator flow path includes a plurality of flow sensor means and a control means for measuring the change in the rate of gas flow and said step of measuring said change in the rate of gas flow comprises measurement at at least one of the sensor means.

10. A system of triggering pressure supported ventilation to a patient supplied with breathing gas from a ventilation system having a source of breathing gas, a patient breathing attachment, an exhalation valve, and a functionally open ventilation flow path in fluid communication with said source of breathing gas, said patient breathing attachment, and said exhalation valve, comprising:

means for delivering breathing gas from said source to said patient breathing attachment at a preinspiratory predetermined continuous rate of flow;

flow sensor means in said flow path for measuring a flow rate of said breathing gas from said source of breathing gas to said patient breathing attachment to determine a gas supply flow rate, and for measuring a flow rate of said breathing gas from said patient breathing attachment to said exhalation valve to determine an exiting gas flow rate;

means responsive to said flow sensor means for determining a patient inspiratory effort in said flow path by comparing said gas supply flow rate with said exiting gas flow rate to determine a flow rate difference due to inhalation thereby indicating patient inspiratory effort, and said means responsive to said flow sensor operative to generate pressure support in said breathing gas delivered from said source to said patient when said flow rate difference due to inhalation exceeds a predetermined threshold value;

means to determine the beginning of the patient's exhalation cycle and means to reduce the flow rate for a predetermined period of time at the beginning of said exhalation cycle; and means for restoring delivery of said breathing gas from said source to said patient breathing attachment at said preinspiratory, predetermined continuous rate of flow before a next patient inspiratory effort.

11. The system of claim 10, wherein said source of breathing gas comprises a plurality of different gas sources, and means for mixing said different gases.

12. The system of claim 11, further including means for controlling the proportions of said different gases in said mixture.

13. The system of claim 10, wherein said flow path includes an inhalation and exhalation flow path into and from said patient breathing attachment, and said inhalation flow path and said exhalation flow path form a wye junction communicating with the patient breathing attachment, and wherein said flow sensor means for measuring the rate of gas flow into said patient breathing attachment is located at said wye junction.

14. The system of claim 13, wherein said sensor is located in the flow path between said wye and said patient breathing attachment.

15. The system of claim 10, wherein said flow path includes an exhalation flow path from said patient breathing attachment, an inhalation flow path to said patient breathing attachment, and said flow sensor means for determining the change in the rate of gas flow into and from said patient breathing attachment comprises at least one flow sensor located in at least one location in said exhalation flow path and at least one other flow sensor in at least one other location in said inhalation flow path.

16. The system of claim 10, further comprising a plurality of flow sensor means and a control means for measuring the gas flow rate at at least one of the flow sensor means.

* * * * *

UNITED STATES PATENT AND TRADEMARK OFFICE
CERTIFICATE OF CORRECTION

PATENT NO. : 5,161,525
DATED : Nov. 10, 1992
INVENTOR(S) : Kimm et al.

It is certified that error appears in the above-identified patent and that said Letters Patent is hereby corrected as shown below:

Col. 4, line 39, after "path" delete the comma --,--.

Col. 5, line 10, after "strategy" insert a period --.--.

Col. 6, line 59, after "breath" delete the period "." and insert therefore a semicolon --;--.

Col. 6, line 62, after "breath" delete the period "." and insert therefore a semicolon --;--.

Col. 6, line 64, after "system" delete the period "." and insert --; and--.

Col. 14, line 1, after first "at" insert a second --at--.

Col. 14, line 2, after first "at" insert a second --at--.

Signed and Sealed this

Twenty-eighth Day of December, 1993

Attest:

BRUCE LEHMAN

Attesting Officer

Commissioner of Patents and Trademarks